United States Patent [19]

Studier et al.

[11] Patent Number: 5,547,843

[45] Date of Patent: Aug. 20, 1996

[54] METHOD FOR PROMOTING SPECIFIC ALIGNMENT OF SHORT OLIGONUCLEOTIDES ON NUCLEIC ACIDS

[75] Inventors: F. William Studier, Stony Brook; Jan Kieleczawa, Coram; John J. Dunn, Bellport, all of N.Y.

[73] Assignee: Associated Universities, Inc., Washington, D.C.

[21] Appl. No.: 325,539

[22] Filed: Oct. 18, 1994

Related U.S. Application Data

[63] Continuation of Ser. No. 916,062, Jul. 17, 1992, abandoned.

[51] Int. Cl.$^6$ .............................. C12Q 1/68; C12P 19/34
[52] U.S. Cl. ...................... 435/6; 435/91.2; 435/91.21; 435/91.5; 935/17; 935/77; 935/78
[58] Field of Search .................... 435/6, 91.2, 91.21, 435/91.5; 935/77, 78, 17

[56] References Cited

U.S. PATENT DOCUMENTS

| | | | |
|---|---|---|---|
| 5,015,569 | 5/1991 | Pontius | 435/6 |
| 5,106,727 | 4/1992 | Hartley | 435/6 |
| 5,114,839 | 5/1992 | Blocker | 435/6 |

OTHER PUBLICATIONS

The Pharmacia Catalog (1989) p. 54..
US Biochemical Catalog, 1990, p. 93.
Szybalski Gene (1990) 90:177–178.
Studier Proc Natl Acad Sci USA (1989) 86:6917–6921.
Schwarz Nucleic Acids Res 1990 18:1079.
Chou Nucleic Acids Res 1992 20:4371.
Sambrook et al. Molecular Cloning: A Laboratory Manual, 1989, p. 8.11.
Drmanac, et al., *Genomics* 4:114–128, (1989).
Poustka, et al., *Cold Spring Harbor Symp. Quant. Biol.* L1:131–139, (1986).
Sequenase Version 2.0 Advertising Literature distributed by United States Biochemical Corporation.
MacFerrin, et al., *Proc. Natl. Acad. Sci.*87:1937–1941, (1990).
Siemieniak and Slightom, *Gene* 96:121–124, (1990).
Studier, "Sequencing With a Library of Primers", Genome Sequencing Conference II, Sep. 30 —Oct. 3, 1990.
Studier and Dunn, "Sequencing With a Primer Library", Speaker Abstract from Department of Energy Human Genome Program Contractor–Grantee Workshop, Feb. 17–20, 1991.
Studier, "Nucleotide Sequencing With a Library of Primers", Abstract Presentation at Cold Spring Harbor Laboratory meeting on Genome Mapping and Sequencing, May 2–6, 1990.

Primary Examiner—W. Gary Jones
Assistant Examiner—Carla Myers
Attorney, Agent, or Firm—Margaret C. Bogosian

[57] ABSTRACT

Disclosed is a method for promoting specific alignment of short oligonucleotides on a nucleic acid polymer. The nucleic acid polymer is incubated in a solution containing a single-stranded DNA-binding protein and a plurality of oligonucleotides which are perfectly complementary to distinct but adjacent regions of a predetermined contiguous nucleotide sequence in the nucleic acid polymer. The plurality of oligonucleotides anneal to the nucleic acid polymer to form a contiguous region of double stranded nucleic acid. Specific application of the methods disclosed include priming DNA synthesis and template-directed ligation.

21 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:1:

GTTGCGCAGC CTGAATGGCG AATGGCGCTT TGCCTGGTTT CCGGCACCAG AAGCGGTGCC        60

GGAAAGCTGG CTGGAGTGCG ATCTTCCTGA GGCCGATACG GTCGTCGT                    108

METHOD FOR PROMOTING SPECIFIC ALIGNMENT OF SHORT OLIGONUCLEOTIDES ON NUCLEIC ACIDS

GOVERNMENT SUPPORT

Work described herein was supported by grants from the United States Government which has certain rights to this invention.

This application is a continuation of Ser. No. 07/916,062, filed on Jul. 17, 1992, now abandoned.

BACKGROUND

Substantial improvement in the efficiency of nucleotide sequencing is needed if the goals of the human genome sequencing project are to be realized. Improvements in sequencing technology would also provide substantial benefit to molecular genetics by liberating creative scientists from the repetitive, but highly informative task of sequencing newly isolated DNAs of interest.

A potentially efficient method of sequencing by current technology is by primer walking. By this technique, priming an enzymatic sequencing reaction within a segment of known sequence (such as vector sequence) is used to extend the sequence into the unknown region. The newly determined sequence in turn is used to select a primer to extend the sequence further, and this process is repeated until the sequence of the entire molecule has been determined. Advantages of primer walking are that the entire sequence can be determined on a single preparation of template DNA without subcloning, and the sequence can be determined in the minimum number of sequencing reactions.

A disadvantage of primer walking has been the inconvenience and expense of having to synthesize a primer for each sequencing reaction. An improvement in priming methods which would eliminate this disadvantage would represent an important advance in the art.

SUMMARY OF THE INVENTION

The subject invention relates to a method for promoting specific alignment of short oligonucleotides on a nucleic acid polymer. The nucleic acid polymer is incubated in a solution containing a single-stranded DNA-binding protein and a plurality of oligonucleotides which are preferably perfectly complementary to distinct but adjacent regions of a predetermined contiguous nucleotide sequence in the nucleic acid polymer. The plurality of oligonucleotides anneal to the nucleic acid polymer to form a contiguous region of double stranded nucleic acid.

Among the important applications of the subject invention is the use of the method for priming nucleic acid polymerization. Prior to contacting the template molecule with an appropriate polymerase enzyme, the nucleic acid template is incubated with a single-stranded DNA-binding protein (SSB) and a plurality (two or more) of nucleotide primers which are perfectly complementary to distinct but adjacent regions of a predetermined contiguous nucleotide sequence in the template molecule. The mixture is incubated under conditions appropriate for annealing of the primers to the predetermined contiguous nucleotide sequence to form a contiguous region of double stranded nucleic acid, and binding of the SSB to the nucleic acid template. The nucleic acid template can be either DNA or RNA.

The priming method described in the preceding paragraph can be employed to prime DNA sequencing reactions by the dideoxynucleotide chain termination method. This novel approach represents a particularly significant advance in the field of DNA sequencing by directed primer sequencing. The conventional approach to directed primer sequencing requires the synthesis of a new oligonucleotide primer designed to anneal near the downstream terminus of a newly determined DNA sequence. This processive approach to DNA sequencing is also known as primer walking.

In the method of this invention, a preexisting oligonucleotide primer library (for example, a hexamer oligonucleotide library) is used as the source of primer to initiate DNA synthesis from the downstream region of a newly determined DNA sequence. A complete library of all possible hexamers would contain 4096 unique hexamer sequences. Sets of these unique primer sequences (for example, a set may contain 3 or 4 unique hexamer sequences) are selected to anneal at a predetermined downstream region of a newly determined DNA sequence to form a contiguous duplex region which will prime specific DNA polymerization. Thus, a single hexamer library can be used to prime literally millions of DNA sequencing reactions thereby obviating the need to generate custom oligonucleotide primers. This improvement will substantially reduce the cost and time associated with large scale DNA sequencing projects.

DETAILED DESCRIPTION OF THE INVENTION

Figure 1:
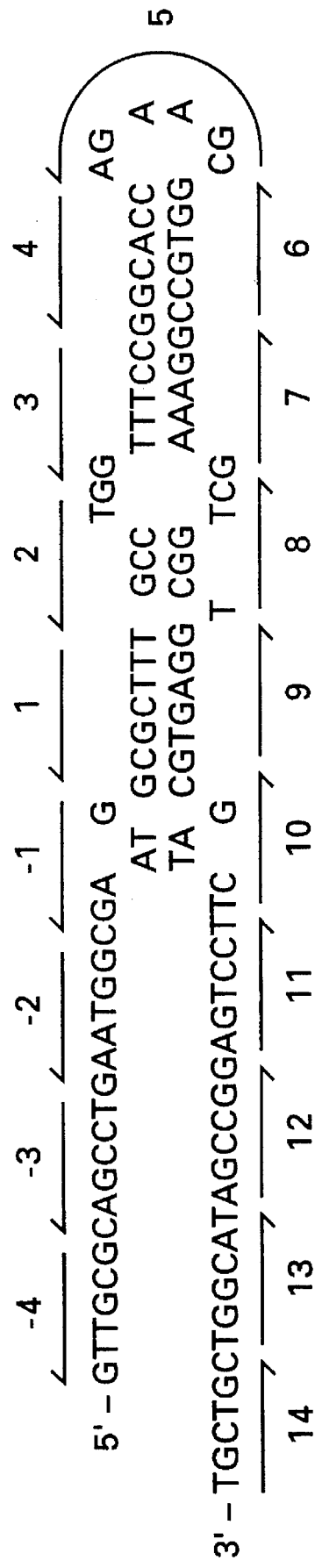
FIG. 1 is a diagram representing the M13mp18 DNA template sequence complementary to hexamer set D, as well as the relative annealing positions of primer set D primers.

The subject invention is based on the discovery that the inclusion of a single-stranded DNA-binding protein in an incubation mixture comprising a nucleic acid polymer, and a plurality (i.e., two or more) of short oligonucleotides complementary to a predetermined contiguous series of nucleotides in the nucleic acid polymer, functions to promote the specific binding of the short oligonucleotides to the predetermined contiguous series of nucleotides in the nucleic acid polymer. The short oligonucleotides are preferably perfectly complementary to distinct but adjacent regions of the predetermined contiguous series of nucleotides.

The methods of this invention are applicable primarily for use in connection with oligonucleotides having a monomer number of between about 5 and 10 (referred to herein as short oligonucleotides) which are prepared by conventional methods. Such oligonucleotides can be labeled with a detectable group, or modified to generate a particular functional group, depending upon the specific application. The methods are applicable for any application in which it is desirable to specifically anneal two or more short oligonucleotides to a contiguous stretch of nucleotides of known sequence in a nucleic acid polymer. As will be discussed in greater detail below, there are a wide variety of such applications.

The expression "nucleic acid polymer" as used herein refers to any nucleic acid molecule having a monomer number which is greater than or equal to the total number of nucleotides in the contiguously annealing set of oligonucleotides. If the polymer is double stranded DNA, the monomer number count is determined by counting the number of nucleotide monomers in a single strand. In practice, the methods of this invention will most often be employed to specifically align a plurality of oligonucleotides at a predetermined contiguous series of nucleotides in a nucleic acid polymer such as genomic DNA isolated from cells or from a genomic DNA library, cDNA from a cDNA library, mRNA, rRNA or restriction fragments of same. The methods are particularly applicable to the analysis of cloned DNA (e.g., M13, cosmid, P1 and YAC clones).

In the past, a problem associated with efforts to promote the specific alignment of two or more short oligonucleotides to a contiguous stretch of nucleotides of known sequence in a nucleic acid polymer has been the occurrence of undesirable oligonucleotide binding events. For example, individual oligonucleotides, or multiples of oligonucleotides can anneal at locations other than the desired location (the contiguous stretch of nucleotides of known sequence in the nucleic acid polymer) in the polymer. In addition, the binding of less than the desired number of contiguously annealing oligonucleotides to the predetermined contiguous nucleotide sequence is an undesirable binding event. The undesirable binding events mentioned are only a few examples of a wide variety of possibilities. These undesirable binding events interfere with the application or assay (e.g., DNA sequencing or template-directed ligation).

It has been determined that the inclusion of SSB in the annealing mixture promotes the specific alignment of short oligonucleotides at the predetermined contiguous nucleotide sequence in the nucleic acid polymer while, at the same time, inhibiting undesirable binding events. This discovery was completely unexpected and is likely to revolutionize DNA sequencing methods.

SSB (single-stranded DNA-binding protein) is a descriptive label which has been applied to a class of proteins which bind more strongly to single-stranded DNA than to double stranded DNA (see e.g., Meyer and Laine, *Microbiological Reviews* 54, 342 (1990); Chase and Williams, *Ann. Rev. Biochem.* 55: 103 (1986)). They tend to be proteins which are involved in DNA metabolism. Specific examples include the *E. coli* SSB, the bacteriophage T4 gene 32 protein and the T7 gene 2.5 protein. The methods of this invention are not limited, however, to the use of the specific SSB examples recited.

SSBs can be used individually, or mixtures of different SSBs can be used. The optimal concentration of SSB can vary depending upon the particular SSB employed, and the nature of the template molecule. This concentration is easily determined empirically by the methods described in detail in the Exemplification section which follows. For example, it has been determined that the optimal ratio for *E. coli* SSB with M13 template is a mass ratio of about 2.5 or greater.

SSB is thought to bind single-stranded DNA by wrapping the DNA around an octamer of SSB, protecting about 145 nucleotides from digestion by DNase but leaving an average of about 30 unbound nucleotides between DNA-octamer beads (Chrysogelos and Griffith, *Proc. Natl. Acad. Sci. USA* 79, 5803 (1982); Griffith et al., *Cold Spring Harbor Symp. Quant. Biol.* 49, 553 (1984)). Although not wishing to be bound by a mechanism, it is possible that these unbound nucleotides are the sites of initial binding of oligonucleotides to the DNA. Random movement of the octamer beads along the DNA strand might well expose all potential binding sites in the DNA and also displace weakly bound oligonucleotides.

A saturating amount of SSB both suppresses binding by individual short oligonucleotides at locations other than the predetermined nucleotide sequence in the nucleic acid polymer and stimulates contiguous annealing of primers at the predetermined nucleotide sequence. Masking of individual binding sites is an important factor in the success of many applications, and presumably increases the effective concentration of oligonucleotides available for binding at the desired location on the polymer.

Clearly, molecular cooperativity plays a role in the formation of a stable complex between contiguously annealing short oligonucleotides and SSB-coated single-stranded DNA. This cooperativity requires that the binding sites be adjacent in the DNA, without any gaps. Therefore, base-stacking interactions between adjacent oligonucleotides must be responsible for stabilizing binding to SSB-coated DNA.

As was mentioned above, methods for the specific alignment of two or more short oligonucleotides to a contiguous stretch of nucleotides of known sequence in a nucleic acid polymer have utility in a wide variety of applications. A few examples are discussed below.

Priming Nucleic Acid Synthesis

The methods of this invention can be used to prime nucleic acid synthesis from a nucleic acid template. Prior to discussing the specifics of the methodology, it is important to highlight the importance of the invention. The methods relate to the use of a plurality of short oligonucleotide primers to prime nucleic acid synthesis. Prior art methods have employed a single oligonucleotide primer to prime such polymerization reactions. The importance of the use of multiple contiguously annealing primers is that specific members of a library of such oligonucleotides can be combined to generate a contiguous region of duplex DNA. It is no longer necessary to custom synthesize primers in order to complement a known DNA sequence. For example, rather than custom synthesizing a nucleic acid primer of 24 nucleotides in length which is complementary to a known template sequence, four hexamers are selected from a pre-existing hexamer library. The four hexamers are perfectly complementary to the known template sequence and anneal to form a duplex region of 24 base pairs in length. The implications of this will be discussed in greater detail below in connection with DNA sequencing.

In the methods for priming nucleic acid synthesis, the nucleic acid template can be either DNA or RNA. Although the experiments discussed in the Exemplification section below are limited to studies of DNA, it is known that SSB binds to RNA as well. In fact, SSB has been used to bind to RNA in order to remove secondary structure for electron microscopy studies (see e.g., Chase and Williams, *Ann. Rev. Biochem.* 55: 103 (1986); Mangel et al. *Proc. Natl. Acad. Sci. USA* 71: 4541 (1974)).

In general, for purposes of priming polymerization, the useful lower limit for the number of base pairs in a duplex region formed by the contiguous annealing of a plurality of primers to a single-stranded nucleic acid template is 12. In such a case, the number of contiguously annealing primers would be 2, each being a hexamer. Any combination of short oligonucleotides (oligonucleotides having a monomer number of between about 5–10, inclusive) which anneal contiguously to form a duplex region of greater than 12 base pairs, can be used in connection with the methods described herein. Preferably, the duplex region which is formed by contiguous annealing is from about 18–24 base pairs in length.

Following the incubation of the template molecule with SSB and the selected oligonucleotide primers, the primed template is incubated with an appropriate polymerase enzyme. For example, if the template is RNA, the polymerase can be an RNA-dependent DNA polymerase. If the template is DNA, the polymerase can be a DNA-dependent DNA polymerase.

The preferred size of the oligonucleotide primer is 6 monomer units. This size is preferred due to considerations of the binding stability and statistical factors relating to library size. A library (i.e., a collection of unique members, with each unique member being specifically accessible) of all possible hexamers would consist of 4096 unique members. As discussed in greater detail below, a practical minimum number for a useful hexamer library is about 1500. It is also possible to optimize an oligonucleotide library to include or exclude primers known to be particularly useful, or particularly troublesome, respectively. For example, base composition can be taken into account when optimizing the composition of a library.

DNA Sequencing

A particularly important application of the methods of this invention is DNA sequencing. Conventional approaches to directed primer sequencing (primer walking) require the synthesis of new oligonucleotide primers to extend a known sequence into an unknown sequence. Primer walking, particularly with contiguously annealing sets of three or four hexamers, should be an efficient way to sequence DNAs of at least 40 kbp directly without subcloning. Almost all hexamers appear likely to be useable, and a library of all 4096 possible hexamers would be manageable. Smaller libraries could also be effective, but a practical minimum would probably be around 1500 hexamers, which would have a 99% chance of providing at least one contiguous hexamer set of three hexamers within a stretch of 100 nucleotides of template DNA, and an 84% chance of providing a contiguous set of four. Synthesis on even the 0.2 μmole scale provides enough primer for thousands of sequencing reactions at an average cost of only pennies per reaction. Once suitable primer libraries are available, they should improve the efficiency of sequencing in individual laboratories as well as in large-scale sequencing centers.

The size limit of template DNA that can be sequenced by direct priming will ultimately be determined by the sensitivity of detection of sequence ladders, because the concentration of priming sites at a given mass concentration decreases with DNA length. Another limitation may be the chance occurrence of sequences that provide secondary priming sites in the DNA, which should increase with DNA length. It has been clearly demonstrated that the methods of this invention are useful for sequencing DNA which has been cloned in a cosmid vector (≈40 kb). It seems likely that the method should also be applicable to the sequencing of DNA which is cloned in higher capacity vectors such as P1 (≈100 kb) and YAC (≈500 kb) cloning vectors.

Currently, about 60–90% of newly selected contiguously annealing hexamer sets provide useful sequence information, and this percentage seems likely to increase as more is learned about how to select the hexamer sets most likely to prime well. Regions of secondary structure that would interfere with priming should be easy to identify in the template DNA and avoid. The success rate might also be increased by using primer sets consisting of a single heptamer flanked by two hexamers. Addition of only a few hundred heptamers to a hexamer library could provide a useful density of such priming sites.

A primer walking strategy allows the complete sequence of both DNA strands to be determined from the minimum possible amount of primary sequence information, and provides complete freedom to choose additional priming sites for resolving ambiguities. The huge burden of subcloning, template preparation, excess sequencing, and sequence assembly imposed by the currently favored shotgun sequencing is eliminated. Since each template is used repeatedly, a battery of templates plus a primer library would allow sequencing reactions to be assembled rapidly enough to saturate any current or easily foreseeable means of analysis. The entire process is susceptible to computer control and automation, which should increase the efficiency of large-scale DNA sequencing at least an order of magnitude over current practice. Sequencing machines based on these principles could operate with little requirement for skilled human intervention, and could provide the capacity and efficiency needed for the success of the Human Genome Project.

Sequencing by Hybridization

The methods of this invention are also likely to be useful for sequencing by hybridization (see e.g., Strezoska et al. *Proc. Natl. Acad. Sci. USA* 88: 10,089 (1991); Khrapko et al., *DNA Sequence* 1: 375 (1991)). In this method, arrays of oligonucleotides are hybridized to larger DNAs, or arrays of larger DNAs are hybridized to oligonucleotides. A current difficulty in applying this method is efficiently discriminating perfectly paired from imperfectly paired hybrids. By using SSB coated DNA the reliability of sequencing by hybridization is likely to be improved. Khrapko et al. had proposed using continuous stacking hybridization for extending the length of sequence that can be read by sequencing by hybridization. The method of this invention would greatly facilitate the oligonucleotide pairing which is essential for this method.

Template-Directed Ligation

Template-directed ligation is a method wherein a plurality of contiguously annealing oligonucleotides (typically two), modified if necessary to provide appropriate functional groups, are incubated with a template molecule which contains a nucleotide sequence which is perfectly complementary to the oligonucleotides. The oligonucleotides anneal to form a contiguous duplex structure. The complex is then contacted with a ligase enzyme which joins the adjacent oligonucleotides through a phosphodiester linkage.

Such a method can be used, for example, in a diagnostic method for the detection of point mutations in DNA (see e.g., Landegren et al., *Science* 241: 1077 (1988)). The inclusion of SSB in an incubation mixture of this type has been clearly demonstrated to improve binding specificities. Thus, the methods herein are applicable to improving the results of template-directed ligation experiments.

EXEMPLIFICATION

Conditions for Priming by Hexamer Oligonucleotides

Standard Conditions.

The template DNA in initial experiments was single-stranded M13 DNA (6407 nucleotides) or the M13mp18 derivative (7250 nucleotides) (Van Wezenbeek et al., *Gene*

11, 129 (1980); Ebright et al., *Gene* 114, 81 (1992)). In an early experiment it was determined that a group of four hexamers, which were perfectly complementary to distinct but adjacent regions of a predetermined contiguous nucleotide sequence of the template molecule (A4-A1, Table 1), primed well. These primers were used to test the range of conditions suitable for specific priming by hexamers. The standard reaction conditions were derived from the protocols for sequencing with Sequenase 2.0 using $^{35}$S label (US Biochemicals) which employs a modified T7 DNA polymerase.

An equilibration reaction contained 0.7 µg of M13 DNA, 3 µg of *E. coli* SSB and 50 pmole of each hexamer (added last) to give a final volume of 10 µl in 40 mM Tris-Cl, pH 7.5, 50 mM NaCl, 10 mM $MgCl_2$ and concentrations of 33 nM M13 DNA, 16 µM SSB monomer, and 5 µM of each hexamer. Reaction mixtures were assembled at room temperature (assembly at 0° C. gave the same results) and equilibrated for at least 5 min at 0° C. (but usually 30 to 60 min for convenience). Labeling was for 5 min at 0° C., adding 6 µl of an ice-cold solution containing 2.5 units of Sequenase, 313 nM each of dCTP, dGTP and dTTP, about 3.5 µCi [α-$^{35}$S]dATP (a slight molar excess over the unlabeled dNTPs) in 10 mM dithiothreitol, 10 mM Tris-Cl, pH 7.5, 0.1 mM EDTA. The termination reaction was for 5 min at 37° C. in the standard Sequenase protocol, and 0.1% sodium dodecyl sulfate was added to the stop solution to prevent SSB from interfering with electrophoresis of the DNA on sequencing gels.

Reaction Solvent.

Although not needed during the equilibration reaction, $MgCl_2$ is needed for Sequenase activity and was added to the equilibration mixture for convenience. Decreasing the $MgCl_2$ concentration to 5 mM reduced labeling of the sequence ladder substantially; increasing it to 20 mM also decreased labeling but less significantly. Reactions seemed rather insensitive to NaCl concentration between 40 and 100 mM. The minimum practical NaCl concentration was 40 mM because of contribution from the stock solutions of SSB. The stock solution of SSB also contributed glycerol, typically a final concentration of 5% in the equilibration reaction.

SSB Concentration.

Similar results were obtained with SSB purified after expression from the cloned gene, and with SSB obtained from two commercial sources (US Biochemicals, Promega). Titration showed that a certain level of SSB is required to stimulate priming at the desired polymerization start point, and to suppress priming at sites other than the desired polymerization start point. In an experiment using 0.6 µg M13 DNA, 1.2 µg SSB was sufficient to stimulate a readable sequence ladder that nevertheless showed significant priming at secondary sites, 1.5 µg SSB almost eliminated this secondary priming, and 1.8–2.5 µg gave equivalent patterns with no apparent secondary priming. Thus, a mass ratio of SSB to DNA of slightly greater than 2.5 appears to provide maximum stimulation of priming by the contiguously annealed hexamer set and essentially complete suppression of secondary priming. This saturating ratio corresponds to about 22 nucleotides of DNA per SSB monomer, 88 per tetramer, or 176 per octamer, consistent with the value of 175 nucleotides per octamer estimated for the beaded form of the SSB-DNA complex (Chrysogelos and Griffith, *Proc. Natl. Acad. Sci. USA* 79, 5803 (1982); Griffith et al., *Cold Spring Harbor Symp. Quant. Biol.* 49, 553 (1984)).

Labeling intensity was maximal from the minimum saturating amount of SSB to a level of at least 3.5 µg per reaction, but decreased somewhat at 5 µg and higher levels. Labeling was almost completely suppressed by 7.5–10 µg of one preparation of SSB but remained substantial with two others. This complete suppression appeared to be reversed upon dilution. The decrease in priming efficiency at high SSB concentrations is not simply due to a higher ratio of SSB to DNA, since diluting the template DNA 4 fold in 5 µg SSB had little effect on labeling (see below). Most of the early experiments used 5 µg SSB, which appears to be slightly higher than the optimal level for stimulating priming by a contiguously annealing hexamer set, but which may be somewhat more effective in suppressing secondary priming.

Hexamer Concentration.

Oligonucleotides were synthesized (1.0 µmole scale) on a MilliGen 8750 DNA synthesizer. Initially, hexamers were purified using Poly-Pac purification cartridges (Glen Research Corp., Sterling, Va.) according to the manufacturer's specifications. However, tests showed that simply removing the dimethoxytrityl group as part of the synthesis procedure, releasing the oligonucleotide from the support with 30% ammonium hydroxide, incubating at 55 ° C. to remove protecting groups, lyophilizing, and dissolving in water produced hexamers that gave equivalent results and this simplified procedure has been employed.

Specific priming by hexamers from the desired polymerization start point depends upon having a high enough concentration of hexamers to displace SSB and pair contiguously to the template at the desired location. About 5 µM of each hexamer appeared to be sufficient to promote maximum intensity and uniformity of labeling of the sequence ladders under the reaction conditions employed. Increasing the concentrations to 10–50 µM showed only marginal improvement. Reducing the hexamer concentration to 2.5 µM reduced the labeling of shorter DNAs in the sequence ladder, indicating a lower frequency of priming during the labeling reaction. Labeling was much reduced at 1 µM and almost undetectable at 0.5 µM, even though this concentration was still a 15-fold molar excess over template.

DNA Concentration.

Reducing the M13 DNA to 150 ng (7 nM) had little effect on the labeling intensity of the sequence ladder, but further reduction to 50 ng (2.35 nM) significantly reduced labeling, and reduction to 15 ng (0.7 nM) reduced it still further. The patterns of labeling upon dilution of the template DNA were similar whether the SSB concentration remained constant or was diluted in parallel with the DNA.

Equivalent labeling patterns were also obtained when the M13 DNA was diluted in the presence of denatured T7 DNA, keeping a total of 0.6 µg of DNA in each reaction mixture. It is not surprising that competing DNA with a 12-fold higher complexity had little effect on priming efficiency at the desired polymerization start point: M13 DNA itself contains 1.5 times as many hexamers as the 4096 that are possible, so further increases in complexity should have little effect on the density of potential interaction sites for individual hexamers.

Reaction Temperature.

Specific priming at the desired polymerization start point decreased markedly as reaction temperature increased: considerable priming remained at 5° C., much less at 10° C., and very little at 15° C. The average length of the DNA chains in the sequence ladder also increased with temperature, consistent with a reduced frequency of priming. This decrease in priming apparently reflects competition between the contiguously annealing hexamer set and SSB for binding the template DNA, as priming decreased little if at all over this temperature range in the absence of SSB.

In the absence of SSB, the dominant sequence at 0° C. reflects priming by the A2 hexamer at nucleotide 4193 of M13 DNA. This pattern is apparent up to 15° C. but not at 25° or 30° C. The changes in priming pattern with increasing temperature in the absence of SSB presumably reflect differences in pairing stabilities of the four different hexamers, and differences in local context or conformation of the template DNA at the different priming sites. A shift to longer DNA chains is evident at temperatures of 15° C. and higher, presumably reflecting a decreasing overall priming efficiency.

Order of Addition.

Equilibration of hexamer binding at the desired position in the template appeared to take place rapidly in the presence of SSB at 0° C.: labeling of sequence ladders was similar when the 5-min labeling reaction was initiated 2.5, 5, 10, 20 or 30 min after hexamers were added to a pre-equilibrated mixture of DNA and SSB, and labeling was only slightly less when initiated immediately after adding the hexamers. Essentially identical patterns and kinetics of labeling were obtained when SSB was added to a pre-equilibrated mixture of DNA and hexamers, indicating that equilibrium is established rapidly with either order of addition.

In one experiment, weak secondary priming was detected when labeling was initiated 5 or 10 min after SSB was added to a pre-equilibrated mixture of DNA and hexamers, but not 20 min after, whereas no secondary priming was observed when the hexamers were added last. Although any differences in sequence ladders due to order of addition appear to be slight, the procedure routinely employed is to add hexamers after SSB to minimize the potential for secondary priming.

Generality of Priming Reaction

Hexamer Priming in M13 DNA.

To test the generality of priming by sets of contiguously annealing hexamers in the presence of SSB, 20 different sets of contiguously annealing hexamers, containing from 4 to 18 contiguous hexamers complementary to 15 different regions of M13 or M13mp18 DNA, were synthesized. The hexamers in the first three sets of Contiguously annealing hexamers (sets A, B and C) are listed in Table 1. Most subsequent sets of contiguously annealing hexamers were built around an already available hexamer whose complement is found at more than one site in M13 DNA. Thus, hexamer B1 is the same as A4, and hexamer C1 is the same as A2. Altogether, these 20 sets contained a total of 119 different hexamers of widely different composition.

TABLE 1

Sequences of hexamers comprising contiguously annealing hexamer sets A, B and C in M13 DNA.

| Number* | Sequence (5'-3') | Position in M13 DNA† | Other Sites‡ |
| --- | --- | --- | --- |
| A6 | ACCCCC | 1194 | 0 |
| A5 | AGCGAT | 1188 | 1 |
| A4 | TATACC | 1182 | 1 |
| A3 | AAGCGC | 1176 | 2 |
| A2 | GAAACA | 1170 | 6 |
| A1 | AAGTAC | 1164 | 3 |
| B6 | TACCTT | 830 | 4 |
| B5 | ATGCGA | 824 | 0 |
| B4 | TTTTAA | 818 | 9 |
| B3 | GAACTG | 812 | 3 |
| B2 | GCTCAT | 806 | 3 |
| B1 | TATACC | 800 | 1 |

TABLE 1-continued

Sequences of hexamers comprising contiguously annealing hexamer sets A, B and C in M13 DNA.

| Number* | Sequence (5'-3') | Position in M13 DNA† | Other Sites‡ |
| --- | --- | --- | --- |
| C6 | TATACA | 4389 | 1 |
| C5 | GTAACA | 4383 | 5 |
| C4 | GTACCT | 4377 | 1 |
| C3 | TTTACA | 4371 | 3 |
| C2 | TCGGGA | 4365 | 0 |
| C1 | GAAACA | 4359 | 6 |

*Numbers decrease in the 5' to 3' direction, so that the hexamer with the lowest number is at the 3' end of a contiguously annealing hexamer set.
†The nucleotide in M13 DNA that is complementary to the 3' nucleotide of the hexamer at the desired polymerization start site. Priming proceeds toward lower numbers.
‡Number of sites in M13 DNA complementary to the hexamer at positions other than the desired annealing location.

In contiguously annealing hexamer sets A, B and C, each single hexamer and every subset of contiguously annealing hexamers of two to six hexamer units in length was tested for ability to prime sequencing reactions in the presence and absence of SSB. In the remaining 17 contiguously annealing hexamer sets, most subsets of contiguously annealing hexamers of two, three and four hexamer units in length were tested in the presence of SSB. A total of 63 contiguously annealing hexamer sets or subsets of two, 70 contiguously annealing hexamer sets or subsets of three, and 55 contiguously annealing hexamer sets or subsets of four were tested in the 19 contiguously annealing hexamer sets excluding set D. Sequence ladders were analyzed to determine the specificity of priming.

In the absence of SSB, sequence ladders were generally weak and ambiguous, whether primed by individual hexamers or by any of the contiguously annealing sets or subsets of hexamers. Exceptions include hexamer A6, which primed moderately well at its single priming site in M13 DNA, and the contiguous pair B3-B2, which primed selectively as a pair even though neither hexamer by itself primed significantly at this site (and each is complementary to three additional sites in M13 DNA).

In the presence of SSB, priming by individual hexamers was almost always strongly suppressed. Priming by some contiguous pairs of hexamers was also suppressed, but about 40% of those tested primed to greater or lesser extents specifically as a pair in the presence of SSB. Examples include the A6-A5 pair, the B3-B2 pair and the C5-C4 pair. Most sets or subsets of contiguously annealing hexamers having a length of three or four hexamer units were stimulated by SSB to prime intensely and specifically at the desired polymerization start point. Sets of more than four hexamers did not seem to offer any advantage.

The sequence ladders obtained in the presence of SSB were usually primed almost exclusively by the hexamer at the 3' end of the contiguously annealing hexamer set, as shown by a shift of the sequence ladder by six nucleotides with the addition or subtraction of a hexamer at the 3' but not the 5' end of the contiguously annealing hexamer set. However, in many cases priming could also be observed by one or two internal hexamers, producing superimposed sequence ladders six nucleotides apart. Substantial amounts of such double priming are evident in the patterns generated by B4-B1, B3-B1, C6-C3, C5-C3 and C4-C1. In a few cases, the 3' hexamer of the contiguously annealing hexamer set primed weakly if at all, and priming was predominantly or almost exclusively at the next hexamer. Thirteen of the 70 contiguously annealing hexamer sets or subsets of three (19%), and 16 of the 55 contiguously annealing hexamer sets or subsets of four (29%) had enough double priming to make reading of the sequence ladder difficult.

Two other problems interfered with determining sequence primed by contiguously annealing hexamer sets; weak priming and priming at secondary sites other than the desired polymerization start site. A few sets of contiguously annealing hexamers primed so weakly that 2–5 day exposures of the autoradiogram were required to read the sequence. Relatively weak priming by several sets of contiguously annealing hexamers of three hexamers increased substantially when a fourth contiguously annealing hexamer was added. Significant interference by priming at secondary sites was observed in three cases affecting 11 contiguously annealing hexamer sets or subsets of three or four hexamer units in length.

Ladders from which sequence could be read unambiguously without difficulty were obtained from 49 of the 70 contiguously annealing hexamer sets or subsets of three hexamer units (70%) and 33 of the 55 contiguously annealing hexamer sets or subsets of four hexamers (60%). At least some sequence information could be obtained from many of the other ladders as well. The most frequent problem, overlapping ladders primed by two or more hexamers in a string, might well be resolvable by computer analysis to generate reliable sequence information.

Interference by Base-pairing in Template DNA.

The set of contiguously annealing hexamer primers referred to as hexamer set D is a special case not included in the above analysis. This set was built from a site complementary to hexamer A3 at nucleotide 6446–6451 in M13mp18 DNA and extended initially to comprise a contiguously annealing set of six hexamers. Unlike the other sets of contiguously annealing hexamers, none of the combinations of these six hexamers primed a sequence ladder from the desired polymerization start site. Examination of the template sequence revealed a perfect 11-base palindrome plus considerable potential for additional base pairing that might compete directly against pairing of these hexamers with template DNA. The M13mp18 DNA template sequence complementary to hexamer set D, as well as the relative annealing positions of primer set D primers, is shown in SEQ. ID. NO: 1.

Hexamer set D was extended in both directions by the addition of contiguously annealing hexamers in an effort to extend the duplex region away from the influence of the intramolecular base-paired structure in the template DNA. It was determined that specific priming was obtained with contiguously annealing hexamer set D14-D11 on the upstream side and set D1'-D4' on the downstream side, whereas set D10-D7, which substantially overlaps the region of potential pairing, did not prime specifically from the desired polymerization start site. Thus, competition from base-pairing in the template DNA seems to prevent priming by hexamer sets.

SSB is thought to remove most base-paired structures from single-stranded DNA (Meyer and Laine, *Microbiological Reviews* 54, 342 (1990)), but the potential structure at the position of contiguously annealing hexamer set D may be too stable to be removed by SSB under the conditions used for priming sequencing reactions. In an effort to remove the secondary structure from the template molecule, the template DNA was heated in the presence of SSB. SSB is known to be very thermostable and the rationale was that heating might allow SSB to stabilize the unfolded structure and stimulate priming. However, heating the mixture of primers, DNA and SSB to temperatures as high as 90° C. before attempting sequencing reactions at 0° C. did not promote specific priming by hexamer string D4-D1. Perhaps the structure in the template DNA can form again after cooling in the presence of SSB, or perhaps displacement of SSB in the process of forming a contiguous hexamer string allows the structure to form and displace the hexamers.

Since structure in the template DNA forms by intramolecular association but contiguously annealed primer sets form by intermolecular associations, it was reasoned that priming might be favored by increasing the concentration of hexamers. However, increasing the hexamer concentration tenfold, from the usual 5 µM to 50 µM was not sufficient to promote specific priming by the primer subset D4-D1.

Although strong local base-pairing in the template DNA seems to prevent priming by hexamer sets, inspection of the sequence of template DNA in the region where priming is desired should allow most such problem areas to be identified and avoided.

Priming by Hexamer Sets in Denatured Double-stranded DNAs.

Conditions for priming by contiguously annealing hexamer sets were developed using the naturally single-stranded M13 viral DNA, but the goal was to prime directly on the single strands from double-stranded DNAs of at least cosmid length (40,000 bp or larger). The contiguously annealing hexamer set A4-A1 primed specifically on heat- or alkali-denatured linear or supercoiled forms of double-stranded M13 DNA, demonstrating that the presence of the complementary strand in the reaction mixture does not prevent specific priming by contiguously annealing hexamer sets. Good sequence ladders were also obtained from a heat-denatured 2.1-kbp PCR product from T7 gene 5.

To test a DNA in the size range of cosmid DNAs, priming was attempted with contiguously annealing hexamer sets at three different regions in T7 DNA. T7 DNA is a linear double-stranded DNA of 39,937 base pairs whose sequence is known. Standard reaction conditions contained 0.6–1 µg of denatured T7 DNA, which provided 2.3–3.8 nM of unique priming sites, a concentration range where the intensity of sequence ladders primed on M13 DNA had decreased but was still substantial. In each region of T7 DNA, contiguously annealing hexamer sets of three or four hexamers primed specific sequence ladders that were usually readable after overnight exposure of the autoradiograms. Some sets of contiguously annealing hexamers primed very weakly or primed double or triple ladders, which represent problems similar to those observed in M13 DNA. Increasing the hexamer concentration as much as 10-fold slightly changed the distribution of priming in a triply primed ladder but did not reduce priming to a single site.

Different procedures were tested for converting T7 DNA to single strands for sequencing reactions. Equivalent sequence ladders were obtained after the following treatments of the DNA: 2 min at 100° C. before adding 10x reaction buffer; 2 min at 100° C. in the presence of SSB (which is highly thermostable); 2 min at 100° C. or 5 min at room temperature in 50 mM NaOH, 50 mM NaCl followed by neutralization at 0° C. In almost all of our experiments, DNA was denatured by heating, either in the presence or absence of SSB.

Since a single strand of T7 DNA is over six times the length of M13 DNA, an experiment was designed to test whether reducing the size of the DNA containing the specific priming site for a contiguously annealing hexamer set would have any effect on priming. Reducing the size to 20, 14, 7 or 4 kbp by cutting the DNA with different restriction enzymes before denaturation had no detectable effect on the sequence ladders obtained.

As an initial test of primer walking with contiguously annealing hexamer sets on a cosmid-sized DNA of unknown sequence, the DNA of LPP-1 was used. LPP-1 is a T7-like cyanobacteriophage (Sherman and Haselkorn, *J. Virol.* 6, 841 (1970)) having a sequence which we had partially determined. To prime synthesis, 34 contiguously annealing hexamer sets, each of four hexamer units in length, were designed to prime within blocks of known sequence and to prime synthesis into unknown regions. These contiguously annealing hexamer sets were chosen at a relatively early stage in the analysis of primary sequence information, and 7 of them were later found to be unsuitable because of sequence errors at the position to which the primers were designed to anneal, or because the sequence chosen was present at more than one site in LPP-1 DNA. Of the remaining 27 sets, 24 have given readable sequence ladders whose quality ranged from fair to excellent. SSB itself was successful in about half of these cases, and addition of T7 gene 2.5 protein produced readable ladders in the others. The longest read from one of these sequencing reactions so far is 461 nucleotides, but the sequencing reactions were not optimized for long reads, and only some reactions have been analyzed under conditions that allow reading as far as possible. We continue to optimize priming by hexamer strings on LPP-1 DNA and expect to complete the sequence entirely by primer walking with contiguously annealing hexamer sets.

SSB Inhibition of Primers of Different Lengths

Priming by contiguously annealing hexamer sets is effective because SSB both stimulates priming by the hexamer sets and suppresses priming by individual hexamers at other sites in the DNA. To explore the limits of the effectiveness of SSB in suppressing priming, a set of oligonucleotides of increasing length was synthesized, which are complementary to M13 DNA at the position of contiguously annealing hexamer set B and have the same 3' nucleotide as hexamer B2. The B2 hexamer has four complementary binding sites in M13 DNA, but the heptamer and longer oligonucleotides have only one perfectly complementary site. Priming by 5 µM oligonucleotide on 0.6 µg of M13 DNA was tested in the presence of 0, 2 or 5 µg SSB under standard reaction conditions.

In the absence of SSB, maximum priming efficiency was reached at primer lengths of 9 or greater; weaker specific priming was seen by the octamer or heptamer, and only very weak priming was apparent for the hexamer. Adding 2 µg SSB only slightly suppressed priming by the heptamer and seemed to enhance priming by the oligonucleotides of lengths 8 to 11. Adding 5 µg SSB rather strongly suppressed priming by oligonucleotides up to length 8, moderately suppressed priming by those of length 9 and 10, and appeared not to suppress priming by those of length 11 and longer. Increasing the temperature to 22° or 37° C. had relatively mild effects, increasing the length of primer needed for maximum efficiency by only one nucleotide or so, and only moderately increasing the suppression by SSB.

Although only one nested set of primers was tested, these results suggest that interaction between contiguous hexamers in a contiguously annealing hexamer set need not be very great to drive the establishment of priming complexes in the presence of SSB.

Nucleotide Sequence of Hexamers in Contiguously Annealing Hexamer Sets

Initially, contiguously annealing hexamer sets were selected without applying specific criteria of base composition or sequence. As more information became available, some sets were built to test the priming behavior of individual hexamers in other sets. The contiguously annealing hexamer sets for LPP-1 DNA were selected to contain hexamers predicted to have a relatively high affinity for template DNA (Breslauer et al., *Proc. Natl. Acad. Sci. USA* 83, 3746 (1986); Quartin and Wetmur, *Biochemistry* 28, 1040 (1989)). In total, more than 200 hexamers have been used in contiguously annealing hexamer sets that primed successfully in more than 45 regions in three different template DNAs. These hexamers have a wide range of sequence and composition.

In analyzing priming behavior in a particular contiguously annealing set of seven hexamers, it was observed that TAATAA did not prime effectively as the 3' hexamer in a contiguously annealing set of three or four hexamers. This hexamer also failed to stimulate priming as the 5' hexamer in a contiguously annealing set of three hexamers, but functioned internally in contiguously annealing sets of three or four. On the basis of this observation, four additional contiguously annealing hexamer sets were built which contained TAATAA or ATTATT. It was determined that both hexamers behaved similarly in each contiguously annealing set. Another contiguously annealing hexamer set happened to contain TTAATT, and this hexamer likewise did not function at the 3' end of contiguously annealing hexamer sets of three or four, but did function internally. Five other hexamers that contained only A and T were used successfully internally in contiguously annealing hexamer sets. The only one of them tested in the 3' position of a set was B4 (Table 1), which performed effectively there and internally. (A determination of whether B4 stimulates priming in the 5' position could not be made because the B3-B2 pair primes effectively by itself.) It is possible that excluding hexamers containing only A and T from the end positions in selecting hexamer sets would improve the probability of successful priming.

Effects of Mismatches

About a dozen instances of secondary priming outside of contiguously annealing hexamer sets in the presence of SSB were identified in which a determination of the specific site of secondary priming could be made. In almost every case, the site of secondary priming was a perfect complement to one of the hexamers in the set of contiguously annealing hexamers, which was flanked by one or more contiguous but mismatched pairing sites for the same hexamer or another hexamer in the mixture. Two cases were also observed where a second sequence ladder was primed six nucleotides past the 3' end of a contiguously annealing hexamer set, and two cases where a second ladder was displaced five nucleotides. When the ladder was shifted by six, one of the hexamers present in the mixture could pair with the six bases immediately past the 3' end of the contiguously annealed hexamer set with a single mismatch; when shifted by five, the five nucleotides at the 3' end of the hexamer could pair with the five bases immediately past the 3' end of the annealed hexamer set.

These observations made it seem likely that a range of contiguous but partially mismatched hexamer sets would be able to prime sequence ladders to some extent in the presence of SSB. To test the effects of mismatches more systematically, all possible single-base mismatches in each of the three hexamers of contiguously annealing hexamer set A3 to A1 were tested for their effect on priming under standard conditions (3 µg SSB). No hexamer with any mismatch in A1, the 3' hexamer of the annealed hexamer set, stimulated priming significantly. On the other hand, eight of the 18 possible mismatches in A2 and 12 of 18 in A3 primed correct sequence, the intensity of the sequence ladder ranging from very weak to moderate. Extending the analysis to other contiguously annealing hexamer sets revealed that all 18 mismatches in B4 primed correct sequence in combination with hexamers B5 and B3, again ranging from very weak to moderate levels. Even more striking, all 18 mismatches in the middle hexamer of yet another contiguously annealing hexamer set primed sequence ladders almost as intensely as the perfectly matched hexamer.

Priming with Contiguously Annealing Sets of Pentamers or Heptamers

If sets of contiguously annealing pentamers would also prime sequencing reactions specifically, the size of the library needed for efficient sequencing would be 4-fold smaller than that needed for hexamers. To test this possibility, a contiguously annealing set of seven contiguous pentamers complementary to M13 DNA at the same position as the hexamer set A was synthesized. Under standard conditions, where contiguously annealing hexamer sets primed intensely, priming by contiguously annealing sets of pentamers could be detected but was relatively weak and ambiguous. Decreasing the reaction temperature to −2.5° C. or −5° C., or increasing the primer concentration 10-fold to 50 μM did not provide much improvement. Pentamer sets alone appear unlikely to be useful in the priming methods described.

Priming with a set of five contiguously annealing heptamers was also tested. T7 DNA was used as template, and the primers were tested individually and in all contiguous combinations, in the presence and absence of SSB. Priming by the individual heptamers was generally weak in the absence of SSB and similar or slightly enhanced in its presence. Contiguous sets of two or more heptamers all stimulated priming from the expected polymerization start point in the absence or presence of SSB. It was observed that the sequence ladders seemed somewhat better in the presence of SSB. A heptamer flanked by two hexamers, and a hexamer flanked by two heptamers primed clean sequence ladders in the presence of SSB.

Other Observations

Modified T7 DNA polymerase (Sequenase) initiates DNA chains preferentially and perhaps exclusively from the 3' hexamer of a contiguously annealing hexamer set. The double and occasionally triple sequence ladders observed invariably arose from priming by the hexamer(s) adjacent to the 3' hexamer in the contiguously annealing hexamer set. The factors influencing the frequency of double priming are not yet well understood but presumably involve relatively weak binding of the 3' hexamer or weak interaction with the rest of the contiguously annealing hexamer set. Three different hexamers containing only A and T residues appeared to prime very poorly as the 3' hexamer in different contiguously annealing hexamer sets. Attempting to eliminate double priming by increasing the concentration of the 3' hexamer has been only marginally effective in the few cases it has been tested.

Although the conditions for priming with contiguously annealed hexamers were worked out with modified T7 DNA polymerase and *E. coli* SSB, other polymerases and other single-stranded DNA-binding proteins might be found to work as well or better. Preliminary experiments indicate that the bacteriophage T4 gene 32 protein and the T7 gene 2.5 protein are both capable of stimulating specific priming by hexamer strings, at least under some conditions, and might offer some advantages in combination with the *E. coli* SSB. If a DNA polymerase and SSB that are both thermostable could prime from contiguously annealed primers, repeated cycles of synthesis and denaturation might be used to obtain sequence ladders from much smaller concentrations of template DNA. Since hexamers sets provide great specificity (there are almost 70 billion possible 18-mers), such amplification might allow sequencing directly on DNAs much larger than cosmids.

Preliminary experiments also indicate that SSB can stimulate template-directed ligation of contiguously annealed short oligonucleotides. Although perhaps offering no advantages over direct priming for DNA sequencing, the ability to ligate short oligonucleotides might be very useful in other applications.

Equivalents

Those skilled in the art will know, or be able to ascertain using no more than routine experimentation, many equivalents to the specific embodiments of the invention described herein. These and all other equivalents are intended to be encompassed by the following claims.

---

We claim:

1. A method for promoting the alignment of a plurality of short oligonucleotides on a single-stranded DNA, comprising:
   a) forming an incubation mixture comprising:
      i) the single-stranded DNA;
      ii) a saturating amount of single-stranded DNA-binding protein; and
      iii) a plurality of short oligonucleotides which are selected to be perfectly complementary to distinct but adjacent regions of a predetermined contiguous series of nucleotides in the single-stranded DNA; and
   b) incubating the incubation mixture under conditions appropriate for:
      i) binding of the single-stranded DNA-binding protein to the single-stranded DNA template; and
      ii) annealing of the oligonucleotides to the distinct but adjacent regions of the predetermined contiguous series of nucleotides in the single-stranded DNA but not to isolated regions of the single-stranded DNA having a nucleotide sequence complementary to only a single oligonucleotide, thereby producing contiguously annealed oligonucleotides.

2. The method of claim 1 wherein the single-stranded DNA-binding protein is selected from the group consisting of the *E. coli* single-stranded DNA-binding protein, the gene 32 protein of bacteriophage T4, the gene 2.5 protein of bacteriophage T7 or combinations of same.

3. A method for priming DNA polymerization at a specific site in a predetermined contiguous series of nucleotides in a single-stranded DNA template, comprising:
   a) forming an incubation mixture comprising:
      i) the single-stranded DNA template;
      ii) a saturating amount of single-stranded DNA-binding protein; and
      iii) a plurality of short oligonucleotides which are selected to be perfectly complementary to distinct but adjacent regions of the predetermined contiguous series of nucleotides in the single-stranded DNA template;
   b) incubating the incubation mixture under conditions appropriate for:
      i) binding of the single-stranded DNA-binding protein to the single-stranded DNA template; and
      ii) annealing of the oligonucleotides to the distinct but adjacent regions of the predetermined contiguous series of nucleotides in the single-stranded DNA template but not to isolated regions of the single-stranded DNA template having a nucleotide sequence complementary to only a single oligonucleotide, thereby producing contiguously annealed oligonucleotides; and
   c) combining the product of step b) with a DNA polymerase enzyme and incubating the resulting combination under conditions appropriate for polymerization initiated at the 3' end of the contiguously annealed oligonucleotides.

4. The method of claim 3 wherein the short oligonucleotides are selected from the group consisting of pentamers, hexamers and heptamers.

5. The method of claim 3 wherein the plurality of short oligonucleotides consists essentially of three hexamers.

6. The method of claim 3 wherein the plurality of short oligonucleotides consists essentially of four hexamers.

7. The method of claim 3 wherein the plurality of short oligonucleotides consists essentially of two hexamers and one heptamer.

8. The method of claim 3 wherein the single-stranded DNA binding protein is selected from the group consisting of *E. coli* single-stranded DNA binding protein, the gene 32 protein of bacteriophage T4, the gene 2.5 protein of bacteriophage T7 or combinations of same.

9. A method for determining the identity and order of nucleotides in a single-stranded DNA template, comprising:
   a) forming an incubation mixture comprising:
      i) the single-stranded DNA template;
      ii) a saturating amount of single-stranded DNA-binding protein; and
      iii) a plurality of short oligonucleotides which are selected to be perfectly complementary to distinct but adjacent regions of a predetermined contiguous series of nucleotides in the single-stranded DNA template;
   b) incubating the incubation mixture under conditions appropriate for:
      i) binding of the single-stranded DNA-binding protein to the single-stranded DNA template; and
      ii) annealing of the oligonucleotides to the distinct but adjacent regions of the predetermined contiguous series of nucleotides in the single-stranded DNA template but not to isolated regions of the single-stranded DNA template having a nucleotide sequence complementary to only a single oligonucleotide, thereby producing contiguously annealed oligonucleotides;
   c) combining the product of step b) with a DNA polymerase enzyme and incubating the resulting combination under conditions appropriate for polymerization initiated at the 3' end of the contiguously annealed short oligonucleotides and for selective chain termination; and
   d) analyzing the products of step c) to determine the identity and order of nucleotides in the single-stranded DNA template.

10. The method of claim 9 wherein the DNA polymerase enzyme is selected from the group consisting of T7 DNA polymerase and modified T7 DNA polymerase.

11. The method of claim 9 wherein the short oligonucleotides are selected from the group consisting of pentamers, hexamers and heptamers.

12. The method of claim 9 wherein the plurality of short oligonucleotides consists essentially of three hexamers.

13. The method of claim 9 wherein the plurality of short oligonucleotides consists essentially of four hexamers.

14. The method of claim 9 wherein the plurality of short oligonucleotides consists essentially of two hexamers and one heptamer.

15. The method of claim 9 wherein the single-stranded DNA binding protein is selected from the group consisting of the *E. coli* single-stranded DNA-binding protein, the gene 32 protein of bacteriophage T4, the gene 2.5 protein of bacteriophage T7 or combinations of same.

16. A method for template-directed ligation of oligonucleotides, comprising:
   a) providing a single-stranded DNA template having a predetermined contiguous series of nucleotides;
   b) forming an incubation mixture comprising:
      i) the single-stranded DNA template;
      ii) a saturating amount of single-stranded DNA-binding protein;
      iii) a plurality of short oligonucleotides which are selected to be perfectly complementary to distinct but adjacent regions of the predetermined contiguous series of nucleotides in the single-stranded DNA template; and
      iv) a DNA ligase; and
   c) incubating the incubation mixture under conditions appropriate for:
      i) binding of the single-stranded DNA-binding protein to the single-stranded DNA template;
      ii) annealing of the oligonucleotides to the distinct but adjacent regions of the predetermined contiguous series of nucleotides in the single-stranded DNA template but not to isolated regions of the single-stranded DNA template having a nucleotide sequence complementary to only a single oligonucleotide; and
      iii) formation of phosphodiester bonds between adjacent oligonucleotides by the DNA ligase.

17. The method of claim 16 wherein the short oligonucleotides are selected from the group consisting of pentamers, hexamers and heptamers.

18. The method of claim 16 wherein the plurality of short oligonucleotides consists essentially of three hexamers.

19. The method of claim 16 wherein the plurality of short oligonucleotides consists essentially of four hexamers.

20. The method of claim 16 wherein the plurality of short oligonucleotides consists essentially of two hexamers and one heptamer.

21. The method of claim 16 wherein the single-stranded DNA binding protein is selected from the group consisting of the *E. coli* single-stranded DNA binding protein, the gene 32 protein of bacteriophage T4, the gene 2.5 protein of bacteriophage T7 or combinations of same.

* * * * *